United States Patent [19]

Vinogradov et al.

[11] Patent Number: 4,566,324

[45] Date of Patent: Jan. 28, 1986

[54] METHOD AND DEVICE FOR DETERMINATION OF RHEOLOGICAL CHARACTERISTICS OF POLYMER AND DISPERSE SYSTEMS

[76] Inventors: Georgy V. Vinogradov, Leninsky prospekt, 70/11, kv. 99, Moscow; Jury F. Deinega, ulitsa Tverskaya, 6, kv. 19, Kiev; Jury G. Yanovsky, Okruzhnoi proezd, 22/64, kv. 92; Olga V. Vasilieva, Michurinsky prospekt, 10, kv. 157, both of Moscow; Alexandr A. Konstantinov, ulitsa Donskaya, 3, kv. 12; Mikhail M. Chernysh, Leninsky prospekt, 44, kv. 143, both of Moscow, all of U.S.S.R.

[21] Appl. No.: 686,217

[22] Filed: Dec. 26, 1984

[30] Foreign Application Priority Data

Jan. 5, 1984 [SU] U.S.S.R. .............................. 3708254

[51] Int. Cl.$^4$ ........................................... G01N 11/14
[52] U.S. Cl. ..................................................... 73/60
[58] Field of Search ...................................... 73/59, 60

[56] References Cited

PUBLICATIONS

Jerrard, H. G., *Apparatus for the Simultaneous Study of Streaming Double Refraction and Viscosity*, in Rev. of Sci. Instr., vol. 26, No. 11, pp. 1007–1017, Nov. 1955.

*Primary Examiner*—Stewart J. Levy
*Assistant Examiner*—Joseph W. Roskos
*Attorney, Agent, or Firm*—Lilling & Greenspan

[57] ABSTRACT

A method for determination of rheological characteristics of polymer and disperse systems, comprising the steps of placing a system to be investigated into a gap between two coaxial cylinders, the first cylinder being rigidly secured on the case of the device, while the second cylinder is rigidly connected to an output shaft of a servo drive, subjecting the system to mechanical deformation by tangentially displacing one of the cylinders in relation to the other conditioned by the restricted shear flow of the system, and exposing the system to an electrical field produced in the gap by connecting a voltage source to the external cylinder provided with butt ends transparent for radiation. The specified deformation and double refraction of the system are measured to determine thereby the rheological characteristics of the system being investigated.

2 Claims, 1 Drawing Figure

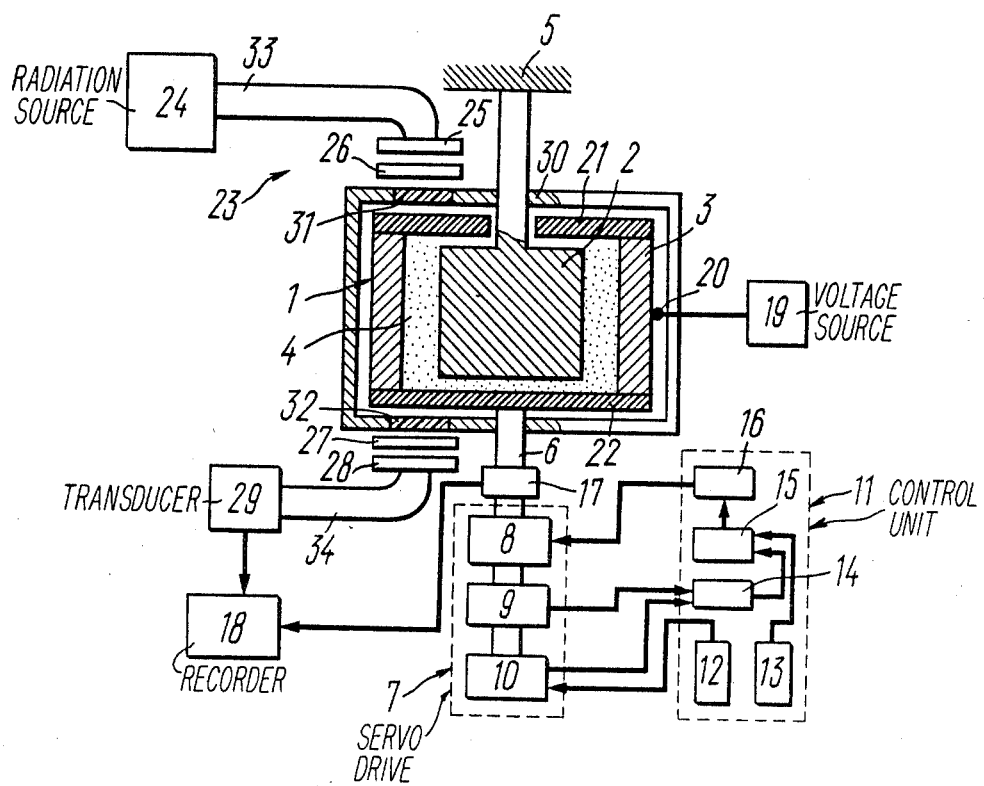

METHOD AND DEVICE FOR DETERMINATION OF RHEOLOGICAL CHARACTERISTICS OF POLYMER AND DISPERSE SYSTEMS

BACKGROUND OF THE INVENTION

This invention relates to determination of properties of fluids and, in particular, to methods for determination of rheological characteristics of polymer and disperse systems and devices therefor.

The invention can be used to study the rheological properties of a broad class of systems based on polymer materials, adhesives, lacquers, pigments and disperse systems, that is in all fields dealing with investigation and simulation of rheological behavior of various materials.

Methods increasingly used at present to analyze the rheological properties of fluids employ the reaction of systems to mechanical deformation in different conditions in the gap between two elements of a measuring unit by tangentially displacing one element in relation to the other. The most frequently used techniques are continuous shear deformation at a constant rate, harmonic oscillations, and superimposition of harmonic oscillations on the continuous shear deformation.

These conditions can generally be described by the following expression: $\dot{\gamma} = \dot{\gamma}_n + \gamma_o \omega \sin \omega t$, where $\dot{\gamma}$ is the total deformation rate, $\dot{\gamma}_n$ is the deformation rate of the steady flow, $\gamma_o$ is the deformation amplitude of periodic deformation, $\omega$ is the circular frequency of periodic deformation, and $t$ is the elapsed time.

When diagonal components of the complete stress tensor are not equal to zero in viscoelastic systems, it is very often because some extremely objectionable phenomena, from the point of view of the processing technology, such as extrudate bulging, elastic turbulence and disturbance of the flow continuity. To control such phenomena, being the forms in which normal stresses are manifested, eliminates problems in processing of viscoelastic systems, such as improvement of quality or increasing the output capacity of equipment. One of the ways to deal with the problem may be the application of forces perpendicular to the flow direction, since it provides an opportunity to control the components of the complete stress tensor in the process of mechanical deformation of investigated systems under the above conditions.

Known in the art is a method for determination of dynamic properties of viscoelastic fluids (cf., for example, Vibratsionnaya Viskoziemtria, Collection of articles published by the Siberian branch of Institut Teplofiziki AN SSSR, Novosibirsk, 1976, A. I. Isayev, A. K. Kulapov, G. V. Vinogradov, Instrument for Determination of Dynamic Characteristics of Viscoelastic Fluids, pp. 91-106) comprising the steps of placing the investigated fluid in the gap between two coaxial cylinders, mechanically deforming said fluid by harmonic oscillations through tangential displacement of one of the cylinders in relation to the other, and measuring the applied deformation. Simultaneously, to be measured is the angular displacement transmitted through the investigated fluid to the other cylinder in relation to which the first cylinder makes its tangential motions. The two quantities obtained serve to determine the rheological properties of the fluid: the complex dynamic shear modulus and its components, such as the modulus of elasticity and the modulus of losses and tangential stress.

Also known in the art is a device realizing said method (cf., for example, Vibratsionnaya Viskozimetriya, collection of articles published by the Siberian branch of Institut Teplofiziki of the Academy of Sciences of the USSR, Novosibirsk, 1976, A. I. Isayev, A. K. Kulapov, G. V. Vinogradov, Instrument for Determination of Dynamic Characteristics of Viscoelastic Fluids, pp. 91 106) comprising a measuring unit composed of two coaxial cylinders arranged with a gap wherein the investigated fluid is placed, the first cylinder being secured to the body of the device, while the second cylinder is rigidly connected with an output shaft of a drive comprising a motor system equipped with reducing and link gears in order to transform the motor rotational motion into the oscillations of the output shaft of the drive, and a transducer to convert the second cylinder angular displacements into electrical signals, which is placed on the output shaft of the drive and is electrically coupled to a recorder. The first cylinder is placed on the shaft so that it is capable of torsional vibrations in relation to said shaft whose one end is rigidly secured to the instrument body and which mounts a transducer of angular displacements of this cylinder into electrical signals, said transducer being also coupled to a recorder.

This method for determination of dynamic characteristics of viscoelastic fluids and the device realizing it have certain limitations. They can determine rheological characteristics of fluids only in harmonic oscillation conditions, since the device has only one fixed position of the motor system in relation to the output shaft of the drive, wherein this output shaft is set into oscillatory motion.

Known in the art is a method for determination of rheological characteristics of polymer and disperse systems (cf., for example, Technical Description and Operational Instructions 1939-00-00-TO of Vibroreometr VR-74. Spetsialnoye Konstruktorskoye Byuro Instituta neftekhimicheskogo sinteza im. A. V. Topcieva AN SSSR, Moscow, 1975) comprising the steps of placing a polymer or disperse system to be studied in a gap between two coaxial cylinders, subjecting said system to mechanical deformation by tangentially displacing one of the cylinders in relation to the other under the conditions of continuous shear deformation at a constant rate, of harmonic oscillations, and of superimposition of harmonic oscillations on continuous shear deformation, and measuring said deformation.

Concurrently, measurements are made of the angular displacement transmitted through the investigated system to the cylinder in relation to which the other cylinder makes tangential displacements. The two quantities are the basis for determination of the rheological characteristics: the complex dynamic shear modulus and its components—the modulus of elasticity and the modulus of losses and shear stress.

Also known is a device to realize the method for determination of rheological characteristics of polymer and disperse systems (cf., for example, Technical Description and Operational Instructions 19139-00-00-TO of Vibroreometr VR-74, published by Spetsialnoye konstruktorskoye byuro Instituta neftekhimicheskogo sinteza im. A. V. Topchieva AN SSSR, Moscow, 1975), comprising a measuring unit composed of two coaxial cylinders made of a current-conducting material and arranged with a gap wherein the investigated viscoelastic system is placed, the first cylinder being secured to the case of the device, while the second is rigidly connected to the output shaft of the drive, which transforms the signal fed from a control unit electrically coupled thereto into the angular displacement of said cylinder, and a transducer to convert the angular displacement of the second cylinder into an electrical signal, said transducer being positioned on the output shaft of the servo drive and coupled to a recorder. The first cylinder of the measuring unit is fixed on the shaft so that it is capable of making torsional vibrations in relation to said shaft whose one end is secured in the case of the device. The shaft also carries the transducer of the angular displacement of this cylinder into an electrical signal, which is coupled to a recorder.

The first cylinder of the measuring unit is held radially by an air bearing which is used to reduce friction when measuring the angular displacement of the first cylinder. The air bearing requires additional equipment items, such as a compressor, air filters, an air pressure regulator and stabilizer. The external cylinder has one butt end open and the investigated system, being placed in the gap between the coaxial cylinders, has one surface thereof in contact with the air.

The method employed to determine rheological characteristics is based on measuring the deformation and angular displacement of the first cylinder of the measuring unit and cannot, therefore, be used to determine normal stresses.

The air exposed surface of the investigated system can, in the process of deformation, lead to a secondary flow in the axial direction and subsequent explusion of the system from the gap.

The device realizing this method is not suitable for measuring normal stresses produced in the process of deformation. Moreover, the measuring unit composed of two coaxial cylinders indeed provides a highly uniform deformation field but gives no means to apply additional forces to the system in the direction perpendicular to the flow by mechanically displacing one cylinder radially in relation to the other cylinder.

In addition, the use of additional equipment supporting the operation of the air bearing makes the device more complicated.

SUMMARY OF THE INVENTION

It is an object of this invention to provide a method for determination of rheological characteristics of polymer and disperse systems and a device therefor in order to determine the rheological characteristics varying due to forces directed perpendicularly to the direction of the restricted shear flow.

Another object of the invention is to widen the scope of properties of a system, which can be determined under the conditions of the restricted shear flow subjected concurrently to forces directed perpendicularly to the direction of said flow.

This is achieved by a method for determination of the rheological characteristics of polymer and disperse systems comprising the steps of placing the polymer or disperse system to be investigated in the gap between two coaxial cylinders, subjecting said system to mechanical deformation by tangentially displacing one cylinder in relation to the other under the conditions of continuous constant-rate shear deformation, harmonic oscillations, and superimposition of harmonic oscillations on the continuous shear deformation, and measuring the deformation. According to the invention, the system is subjected to mechanical deformation in the restricted shear flow and to an electrical field whose lines are perpendicular to the system flow direction and whose intensity does not exceed the breakdown strength of the system, the double refraction of the system is measured while it is subjected to mechanical deformation and the force of the electrical field, the magnitude of deformation and double refraction being indicative of the rheological characteristics of the system.

This is also achieved in that a device for determination of rheological characteristics of polymer and disperse systems, comprising a measuring unit composed of two coaxial cylinders made from a current-conducting material and arranged with a gap wherein the system to be investigated is placed, the first cylinder being secured to the case of the device, while the second cylinder is rigidly connected to an output shaft of a servo drive which transforms the signal fed from a control unit electrically coupled thereto into the angular displacement of this cylinder, and a transducer of the angular displacement of the second cylinder into an electrical signal, which is set on the output shaft of the servo drive and connected to a recorder, according to the invention, comprises a voltage source connected to a side surface of the external cylinder having transparent butt ends, and a double refraction measuring unit having a radiation source, and, arranged downstream, a polarizer, two plates whose thickness is divisible by an uneven number of quarter wavelengths of the radiation, which are arranged on both sides of the butt ends of the external cylinder of the measuring unit in the zone where the system under investigation is located, an analyzer, and a transducer of radiation into an electrical signal, which is connected to a recorder, the first cylinder of the measuring unit being rigidly secured to the case of the device.

The method for determination of rheological characteristics of polymer and disperse systems permits the system under investigation, which is exposed to mechanical deformation under the conditions of the restricted shear flow, to be subjected to additional forces applied in the direction perpendicular to the direction of the flow.

The device realizing the method according to the invention permits determination of normal stresses produced in the process of deformation of the system under investigation. In addition, the design of the device becomes much simpler.

BRIEF DESCRIPTION OF THE DRAWINGS

FIG. 1 is a schematic illustration in partial cross-section of the device for determining rheological characteristics of polymer and disperse systems.

DETAILED DESCRIPTION OF THE INVENTION

Below is a detailed description of an exemplary embodiment of the present invention, with references to examples and the accompanying drawing wherein a schematic illustration of the device for determination of rheological characteristics of polymer and disperse systems is shown as a longitudinal section view of a measuring unit thereof placed in a constant-temperature cabinet.

A method for determination of rheological characteristics of polymer and disperse systems comprises the steps of placing the polymer or disperse system to be investigated in the gap between two coaxial cylinders, subjecting said system to mechanical deformation by tangential displacement of one cylinder in relation to the other using such techniques as continuous constant-rate shear deformation, harmonic oscillation, and superimposition of harmonic oscillations upon continuous shear deformation in conditions of the restricted shear flow, concurrently exposing the system to an electrical field whose force lines are perpendicular to the direction of the flow and whose intensity does not exceed the breakdown strength of the system. To be measured are the specified deformation and double refraction of the system subjected to mechanical deformation in accordance with a specific principle and exposed to the action of the electrical field. These quantities constitute the basis on which the rheological characteristics of the system under investigation are found according to the following equations:

1. The maximum tangential stress—$\tau_{max}$:

$$\tau_{max} = n \cdot \tau_n / \sin\psi$$

where
 n—whole isochrome order;
 $\psi$—phase shift between the zero isochrome and the first order isochrome;
 $\tau_n = \lambda/2cW$—band factor;
 $\lambda$—radiation wavelength;
 c—flow birefringence coefficient;
 W—thickness of the layer of the system under investigation along the cylinder generating line.

2. The complex dynamic shear modulus—$|G^*|$:

$$|G^*| = \tau_{max}/\gamma_a$$

where
 $\gamma_a$—amplitude of the specified deformation.

3. Modulus of elasticity—$G'$:

$$G' = |G^*|\cos\phi$$

where
 $\phi$—phase shift between the zero isochrome and the specified deformation.

4. Loss modulus—$G''$:
$$G'' = |G^*|\sin\phi$$

5. The permanent component of the first difference of normal voltages—$\delta_c$:

$$\delta_c = \Delta n_c(\lambda/2CH)$$

where
 $\Delta n_c$—permanent component of the double refraction;
 H—thickness of the layer of the system under investigation in the radial direction.

A device for determination of rheological characteristics of polymer and disperse systems comprises a measuring unit 1 composed of two coaxial cylinders 2 and 3 made from a current-conducting material and arranged with a gap wherein a system 4 to be investigated is placed. The first cylinder 2 is rigidly secured on a case 5 of the device, while the second cylinder 3 is rigidly connected to an output shaft 6 of a servo drive 7 which turns on an actuator 8, a tachometer generator 9, and an error sensor 10, which are all mounted on one shaft. The servo drive 7 transforms the signal fed from a control unit 11 electrically connected thereto into the angular displacement of the cylinder 3. The control unit 11 comprises two two-phase generators 12 and 13 which produce signals of specified shapes, a first adder 14, a second adder 15, and a power amplifier 16. The generator 12 is electrically connected to the error sensor 10 whose output is connected to an input of the first adder 14 whose second input is connected to an output of the tachometer generator 9. The output of the first adder 14 is connected to an input of the second adder 15 whose other input is connected to an output of the second generator 13. The output of the second adder 15 is connected to an input of the power amplifier 16 whose output is connected to the actuator 8 of the servo drive 7. A transducer 17 of the angular displacement of the second cylinder into an electrical signal is mounted on the output shaft 6 of the servo drive 7 and connected to a recorder 18.

The device according to the invention also comprises a voltage source 19 connected by means of a contact 20 to the side surface of the external cylinder 3 having butt ends 21 and 22 thereof made from a dielectric material transparent for radiation. A unit 23 for measuring the double refraction of the system comprises a radiation source 24 (a laser, for example) and, arranged downstream, a polarizer 25, two plates 26 and 27 whose thickness is divisible by the uneven number of quarter-wavelengths of the radiation and which are positioned on both sides of the butt ends 21 and 22 of the cylinder 3 in the zone of location of the system 4, an analyzer 28, and a radiation-to-signal transducer 29 (a photomultiplier tube, for example) connected to the recorder 18. This recorder 18 is a system comprising, for example, two analog-to-digital converters, a microcomputer, and a printer.

The measuring unit 1 of the device is enclosed in a temperature-controlled cabinet 30 having windows 31 and 32 located on both sides of the butt ends 21 and 22 of the cylinder 3 in the zone of location of the system 4. The radiation from the source 24 is transmitted to the polarizer 25 through a light pipe 33, and from the analyzer 28 to the transducer 29 through a light pipe 34.

The device for determination of rheological characteristics of polymer and disperse systems operates as follows.

When the technique of superimposition of harmonic oscillations upon continuous shear deformation, described by the equation $\dot{\gamma} = \dot{\gamma}_n + \gamma_o\omega\sin\omega t$, is used, the output signal of the generator 12 producing signals of specified shape in order to maintain conditions for continuous shear deformation is fed to the input of the error sensor 10 of the servo drive 7, and from the output thereof to one of the inputs of the first adder 14. Concurrently, an output damping signal of the tachometer generator 9 is supplied to the second input of the adder 14. The output signal of the first adder 14 is supplied to one input of the second adder 15 and, simultaneously, the output signal of the generator 13, which produces signals of specified shape in order to maintain conditions of harmonic oscillations, is delivered to the other input of the second adder 15 which takes the sum of the two signals—the continuous constant-rate shear deformation and harmonic oscillations. The output signal of the second adder 15 is fed to the input of the power amplifier 16. An amplified signal is transmitted from the output of the power amplifier 16 to the input of the actuator 8 of the servo drive 7. At this stage the output shaft 6 together with the rigidly mounted thereon units, such as the second cylinder 3 of the measuring unit 1 and the transducer 17 of the angular displacement of the second cylinder into an electrical signal, are set into a rotary-oscillatory motion. The output signal of the transducer 17, which is the function of the periodic deformation amplitude, is supplied to one of the inputs of the recorder 18. In this case, the system 4 under investigation, which is placed in the gap between the coaxial cylinders 2 and 3, is subjected to deformation when harmonic oscillations are superimposed on the continuous shear deformation in conditions of the restricted shear flow since the external cylinder 3 is provided with butt ends 21 and 22. Stresses caused by deformation under the above described conditions in the system 4 can be found by measuring the double refraction of this system 4.

Simultaneously, voltage is supplied from the source 19 via the contact 20 to the cylinder 3 and an electrical field is set between the cylinders 2 and 3. The intensity of this electrical field varies with the potential applied and the gap between the cylinders 2 and 3 and the force lines of this field are perpendicular to the flow of the system 4. In consequence, additional radial stresses appear in the system 4 due to orientation and deformation moments.

Radiation from the source 24 is at the same time transmitted via the light pipe 33 to the polarizer 25 and further on to the plate 26 so that it is subjected to circular polarization. Polarized radiation is transmitted through the window 31 of the temperature-controlled cabinet 30, the system 4, along the cylinders 2 and 3, the window 32 of the temperature-controlled cabinet 30 to be delivered to the second plate 27 and to the analyzer 28. It is further transmitted from the analyzer 28 along the light pipe 34 to the transducer 29 whose output electrical signal is fed to the recorder 18 as it is the function of the radiation intensity.

The output radiation intensity of the analyzer 28 is the function of the double refraction of the system 4.

Signals of the transducers 17 and 20 are indicative, respectively, of the deformation to which the system 4 is subjected and the double refraction thereof, which is the function of the stresses in the system 4. These signals are supplied to the recorder 18 in order to determine, using the above equations, the complex dynamic shear modulus and its components, such as the tangential and normal stresses of the system 4 which is subjected to deformation by superimposing harmonic oscillations on the continuous shear deformation in conditions of the restricted shear flow being simultaneously exposed to forces directed perpendicularly to the direction of said flow.

When the harmonic oscillation technique described by the equation $\gamma = \dot{\gamma}_n + \gamma_o \omega \sin \omega t$ is used, the device operates as follows.

The output signal of the error sensor 10 of the servo drive 7 is applied to one input of the first adder 14, while the output damping signal of the techometer generator 9 is applied to the other input thereof. The output signal of the first adder 14 is fed to one input of the second adder 15, while the output signal of the second generator 13 maintaining the harmonic oscillation conditions is fed to the other input thereof. The output signal of the second adder 15 is supplied to the input of the power amplifier 16 and, from the output thereof, the built-up signal is supplied to the input of the actuator 8 of the servo drive 7. The output shaft 6 together with the second cylinder 3 of the measuring unit 1 and the transducer 17 are set into the oscillating motion. The system 4 in the gap between the cylinders 2 and 3 is subjected to deformation by harmonic oscillations in conditions of the restricted shear flow.

The processes describing the effect of the electrical field and measuring of the specified deformation and double refraction are analogous to those in the conditions of superimposition of harmonic oscillations on the continuous shear deformation. Under the harmonic oscillation conditions the proposed device permits determination of the complex dynamic shear modulus, its components, normal and tangential stresses in accordance with the above given equations.

When the continuous constant-rate shear deformation described by the equation $\dot{\gamma} = \dot{\gamma} = $ const. is used, the device operates as follows.

The output signal of the generator 12, controlling the rotation, is supplied to the input of the error sensor 10 of the servo drive 7 and, from the output thereof, to one of the inputs of the first adder 14 whose second input receives the output damping signal of the tachometer generator 9. The output signal of the first adder 14 is supplied to the input of the second adder 15 and, from the output thereof, to the power amplifier 16. The signal is further delivered, from the output of the power amplifier 16, to the input of the actuator 8 of the servo 7. The output shaft 6 together with the second cylinder 3 and the transducer 17 of the angular displacement of the second cylinder into an electrical signal is set into rotary motion. The system 4 in the gap between the cylinders 2 and 3 is subjected to deformation under continuous constantrate shear deformation in conditions of the restricted shear flow.

The processes describing the effect of the electrical field and measurements of the specified deformation and double refraction is analogous to those in the previous conditions. Operating under the continuous constantrate shear deformation conditions, the device according to the invention permits determination of tangential and normal stresses.

For better understanding the method for determination of rheological characteristics of polymer and disperse systems according to the invention is hereinbelow illustrated by examples.

EXAMPLE 1

The task was to determine the rheological characteristics of a flexible-chain polymer—narrow molecular-weight distribution polybutadiene—in conditions of superimposition of harmonic oscillations on the continuous shear flow in accordance with the principle described by the equation $\dot{\gamma} = \dot{\gamma}_n + \gamma \omega \sin \omega t$, and simultaneous exposure to the electrical field. The polybutadiene molecular mass is 180,000. The breakdown voltage is not lower than $10^8$ v/m. The circular frequency of periodic deformation $\omega = 0.06$ s$^{-1}$. The harmonic oscillation amplitude is 1°. The deformation velocity of the steady flow $\dot{\gamma}_n = 0.32$ s$^{-1}$. The electrical field intensity $E = 6 \cdot 10^6$ v/m. Temperature 25° C. Measured were the deformation amplitude $\gamma_a$ and the double refraction characterized by the angle $\phi$ of the phase shift $\psi$ between deformation and the zero isochrome, and the angle $\psi$ of the phase shift between the zero isochrome and the first order isochrome. These figures were used to determine the rheological characteristics of polybutadiene in accordance with the above given equations:

1. The maximum tangential stress $\tau_{max} = 1.585 \cdot 10^5$ Pa.
2. The complex dynamic shear modulus $|G^*| = 2.12 \cdot 10^5$ Pa.
3. The modulus of elasticity $G' = 1.43 \cdot 10^5$ Pa.

4. The modulus of loss $G''=1.55 \cdot 10^5$ Pa.
5. The permanent component of the first difference of normal stresses $\delta_c=2.79 \cdot 10^5$ Pa.

EXAMPLE 2

The task was to determine the rheological characteristics of polyisoprene having a molecular mass of 150,000 in harmonic oscillation conditions in accordance with the principle described by the equation $\dot{\gamma}=\gamma_0\omega \sin \omega t$, and simultaneous exposure to an electrical field having the strength of $E=4.10^6$ V/m at 25° C.

The breakdown voltage of polyisoprene is not lower than $10^9$ V/m.

The circular frequency of oscillations $\omega=1$ s$^{-1}$.

The amplitude of oscillations 20'.

Measured were quantities indicated in the Example 1 and, using the equations given above, rheological characteristics of polyisoprene were found:
1. The maximum tangential stress $\tau_{max}=8.4 \cdot 10^4$ Pa
2. The complex dynamic shear modulus $|G^*|=2.14 \cdot 10^5$ Pa
3. The elasticity modulus $G'=1.99 \cdot 10^5$ Pa.
4. The loss modulus $G''=7.95 \cdot 10^4$ Pa.
5. The permanent component of the first difference of normal stresses $\delta_c=2.97 \cdot 10^5$ Pa.

EXAMPLE 3

The task was to determine the rheological characteristics of narrow molecular-weight distribution polybutadiene having a molecular mass of 83,000 in conditions of the continuous constant-rate shear deformation ($\dot{\gamma}=\dot{\gamma}_n=1$ s$^{-1}$) and simultaneous exposure to an electrical field having the strength of $E=9 \cdot 10^5$ V/m.

The breakdown voltage of polybutadiene is not less than $10^8$ V/m.

Measured was the double refraction of polybutadiene and the resulting figure was used to determine the following quantities:
1. The maximum tangential stress $\tau_{max}=3.98 \cdot 10^4$ Pa.
2. The first difference of normal stresses $\delta_c=7.3 \cdot 10^4$ Pa.

EXAMPLE 4

The task was to determine the rheological characteristics of a disperse system: polybutadiene filled with glass spheres (1 per cent by weight, diameter $4 \cdot 10^{-5}$ m), in conditions of continuous constant-rate shear deformation ($\dot{\gamma}=\dot{\gamma}_n=0.59$ s$^{-1}$) and simultaneous exposure to an electrical field having the strength of $4 \cdot 10^5$ V/m at 25° C.

The breakdown voltage of the system is not lower than $10^8$ V/m.

The molecular mass of polybutadiene is 180,000.

Measured was the double refraction of the system and the resulting figure used to determine the following quantities:
1. The first difference of normal stresses $\delta_c=5.21 \cdot 10^4$ Pa.
2. The maximum tangential stress $\tau_{max}=2.818 \cdot 10^4$ Pa.

EXAMPLE 5

The task was to determine the rheological characteristics of a disperse system comprising polyisoprene and aerosil (one per cent by weight) in conditions of harmonic oscillations ($\dot{\gamma}=\gamma_0\omega \sin \omega t$) and simultaneous exposure to an electrical field having the strength of $E=3 \cdot 10^5$ V/m at 25° C.

The molecular mass of polyisoprene is 150,000.

The circular frequency of oscillations $\omega=0.25$ s$^{-1}$.

The amplitude of oscillations 20'.

Measured were the quantities indicated in the Example 1 to determine the following:
1. The maximum tangential stress $\tau_{max}=1.064 \cdot 10^5$ Pa.
2. The complex dynamic modulus of shear $|G^*|=4.36 \cdot 10^5$ Pa.
3. The elasticity modulus $G'=4.21 \cdot 10^5$ Pa.
4. The loss modulus $G''=1.14 \cdot 10^5$ Pa.
5. The permanent component of the first difference of normal stresses $\delta_c=6.25 \cdot 10^5$ Pa.

EXAMPLE 6

The task was to determine the rheological characteristics of a disperse system comprising polybutadiene and aerosil (one weight percent) in conditions of superimposition of harmonic oscillations on the continuous constant-rate shear deformation ($\dot{\gamma}=\dot{\gamma}_n+\gamma_0\omega \sin \omega t$) and simultaneous exposure to an electrical field having the strength $E=6 \cdot 10^5$ V/m at 25° C.

The breakdown voltage of the system is not lower than $10^8$ V/m.

The circular frequency of oscillations $\omega=0.05$ s$^{-1}$.

The amplitude of oscillations 1°.

The steady flow velocity $\dot{\gamma}_n=0.30$ s$^{-1}$.

Measured were the characteristics indicated in the Example 1 to determine the following:
1. The maximum tangential stress $\tau_{max}=3.12 \cdot 10^5$ Pa.
2. The complex dynamic shear modulus $|G^*|=4.47 \cdot 10^5$ Pa.
3. The elasticity modulus $G'=3.1 \cdot 10^5$ Pa.
4. The loss modulus $G''=3.18 \cdot 10^5$ Pa.
5. The permanent component of the first difference of normal stresses $\delta_c=5.42 \cdot 10^5$ Pa.

The method for determination of rheological characteristics of polymer and disperse systems and a device realizing this method according to the invention can be used for practical laboratory investigations on a broad scale because they can help obtain information on the rheological behavior of systems in conditions of the restricted shear flow under various types of mechanical deformations and simultaneous exposure to forces perpendicular to the shear flow, and for investigating the effect of an electrical field on the rheological behavior of different systems.

What is claimed is:

1. A method for determination of rheological characteristics of polymer and disperse systems comprising the steps of:
    (a) placing one of said systems to be investigated in a gap between a first and a second coaxial cylinder;
    (b) subjecting said system to mechanical deformation of a restricted shear flow by tangentially displacing said first cylinder in relation to said second cylinder and applying three conditions, the first of said conditions including a continuous constant-rate shear deformation, a second condition including harmonic oscillations, and a third condition including a superimposition of harmonic oscillations of said shear deformation at a continuous rate;
    (c) exposing said system to an electrical field having force lines which are perpendicular to a direction of a flow of said system and whose intensity does not exceed a breakdown strength of said system; and
    (d) measuring a magnitude of a double refraction of said system exposed to said mechanical deformation, said electrical field force and said applied magnitude of deformation to determine the rheological characteristics of said system.

2. A device for determination of rheological characteristics of polymer and disperse systems comprising:
(a) a housing
(b) a measuring unit having first and second coaxial cylinders made from a current-conduction material, said first cylinder rigidly secured to said housing and said second cylinder having a side surface and separated from said first cylinder by a gap;
(c) a servo drive having an output shaft rigidly connected to said second cylinder of said measuring unit;
(d) a control unit electrically connected to said servo drive and transforming an electrical signal produced by said control unit into an angular displacement of said second cylinder;
(e) a first transducer mounted on said output shaft of said servo drive and converting said angular displacement of said second cylinder into an electrical signal;
(f) a recorder connected to said first transducer and recording said electrical signal;
(g) a voltage source connected to said side surface of said second cylinder;
(h) a unit connected to said recorder measuring a double refraction of said system;
(i) a source of radiation of said unit;
(j) a polarizer attached to a side of said source of radiation near said unit;
(k) a first plate having a thickness divisible by an uneven number of quarter-wavelengths of said radiation and positioned between said polarizer and a first butt end of said second cylinder in an area where said system is located, said first butt end being transparent to pass said radiation;
(l) a second plate having a thickness divisible by said uneven number of quarter-wavelengths of said radiation and positioned beneath a second butt end of said second cylinder in a path of said radiation, the said second butt end being transparent to pass said radiation;
(m) an analyzer positioned beneath said second plate and measuring an intensity of said radiation traveling through the second plate to the analyzer; and
(n) a second transducer connected by one end to said second plate and by a second end to said recorder, the transducer converts said radiation to an electrical signal and feeds it to the recorder.

* * * * *